US00PP30976P2

(12) United States Plant Patent
Nishita

(10) Patent No.: US PP30,976 P2
(45) Date of Patent: Oct. 22, 2019

(54) ***PORTULACA* PLANT NAMED 'SAKPOR018'**

(50) Latin Name: *Portulaca oleracea*
Varietal Denomination: SAKPOR018

(71) Applicant: Sakata Seed Corporation, Yokohama (JP)

(72) Inventor: Koichi Nishita, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 15/932,886

(22) Filed: May 14, 2018

(51) Int. Cl.
*A01H 5/02* (2018.01)
*A01H 6/30* (2018.01)

(52) U.S. Cl.
USPC ..... Plt./471
CPC ..... *A01H 6/30* (2018.05)

(58) Field of Classification Search
USPC ..... Plt./471
See application file for complete search history.

(56) References Cited

PUBLICATIONS

UPOV hit on *Portulaca* plant named, 'Sakpor018', JP PBR 32469, application date Oct. 5, 2017.*

* cited by examiner

*Primary Examiner* — Anne Marie Grunberg
(74) *Attorney, Agent, or Firm* — Bethany R. Roahrig; Cochran Freund & Young LLC

(57) ABSTRACT

A *portulaca* plant particularly distinguished by having white flowers, long flower blooming period and a dense, compact, and mounding plant growth habit, is disclosed.

2 Drawing Sheets

Genus and species: *Portulaca oleracea.*
Variety denomination: 'SAKPOR018'.

BACKGROUND OF THE NEW PLANT

The present invention comprises a new and distinct variety of *portulaca* plant, botanically known as *Portulaca oleracea*, and referred to by the variety name 'SAKPOR018'.

'SAKPOR018' originated from a hybridization made in October 2010 in Kakegawa, Japan. The female parent was an unpatented proprietary *Portulaca* breeding line named '7B1-23A-V1' which had white, small-sized flowers and a domed plant growth habit. The male parent was an unpatented proprietary *Portulaca* breeding line named '7B1-25A-V1', characterized by its medium-sized white flowers, good petal quality, long blooming time, and upright plant growth habit.

The $F_1$ seeds were sown in May 2011 and ten plants were cultivated. In August 2011, five plants were selected from the $F_1$ group. In October 2011, $F_2$ seeds were harvested after crossing within the five plants. The plants were grown and evaluated, and plant line 'SAKPOR018' was selected in August 2012 for its white, medium-sized flowers, long blooming time, strong blooming power and domed habit.

In March 2013, line 'SAKPOR018' was vegetatively propagated and cultivated in Kakegawa, Japan. In August 2013, the breeder confirmed that line 'SAKPOR018' was fixed and stable. 'SAKPOR018' was propagated and cultivated again in Kakegawa, Japan from 2014 to 2017 to reconfirm the line's stability. 'SAKPOR018' was found to reproduce true to type in successive generations of asexual propagation.

SUMMARY

The following are the most outstanding and distinguishing characteristics of this new variety when grown under normal horticultural practices in Salinas, Calif.

1. White flower color;
2. Long flower blooming period; and
3. A dense, compact, and mounding plant growth habit.

DESCRIPTION OF THE PHOTOGRAPHS

This *portulaca* plant is illustrated by the accompanying photographs which show the plant's overall plant habit including form, foliage, and flowers. The photographs are of a three month old plant grown in Salinas, Calif. under greenhouse conditions. The colors shown are as true as can be reasonably obtained by conventional photographic procedures.

DESCRIPTION OF THE NEW VARIETY

Figure 1:
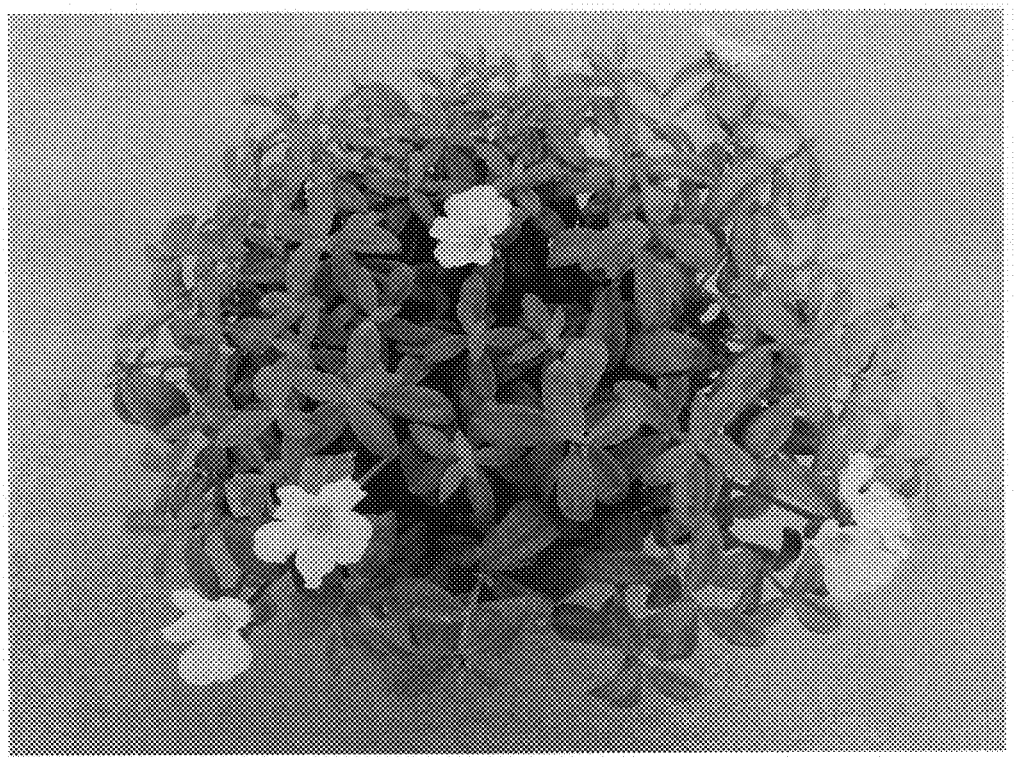
FIG. 1 shows the overall plant habit of the plant grown in a pot.
Figure 2:
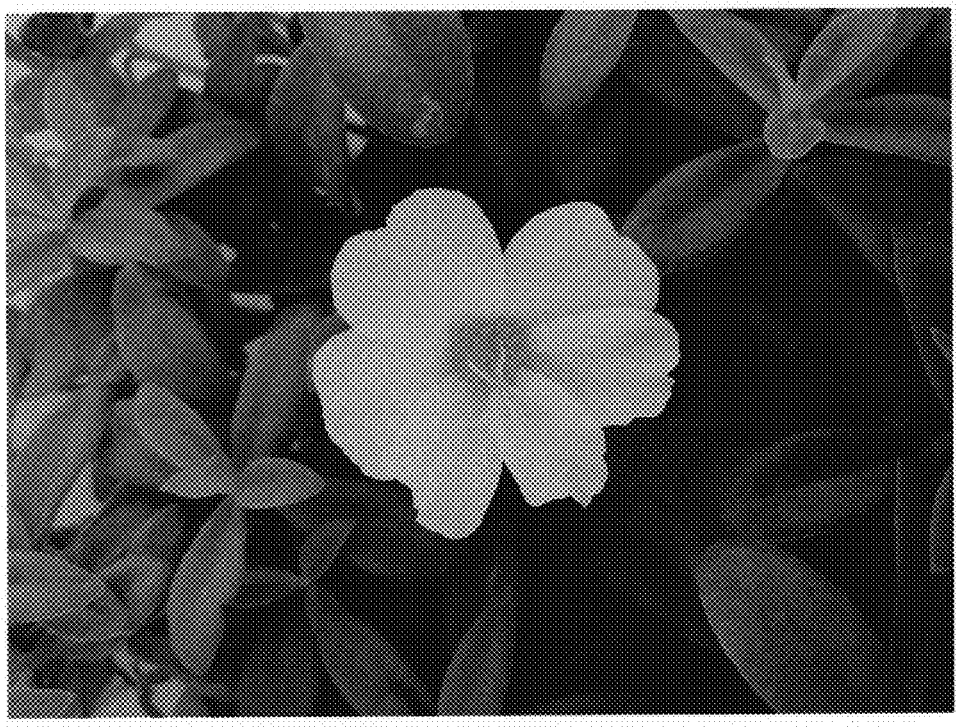
FIG. 2 shows a close-up of the mature inflorescence of the plant.

The following detailed descriptions set forth the distinctive characteristics of 'SAKPOR018'. The data which define these characteristics were collected from three month old plants grown in Salinas, Calif. Color references are to The R.H.S. Colour Chart of The Royal Horticultural Society of London (R.H.S.), $4^{th}$ edition (2001).

Classification:

*Family.*—Portulacaceae.
*Botanical.*—*Portulaca oleracea.*

*Common*.—Purslane.
*Designation*.—'SAKPOR018'.

Parentage:
*Female parent*.—'7B1-23A-V1' (unpatented).
*Male parent*.—'7B1-25A-V1' (unpatented).

Growth:
*Time to produce a rooted cutting*.—About 2 weeks.
*Environmental conditions for plant growth*.—The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:
*Habit and form*.—Dense, compact, and mounding.
*Height*.—Approximately 10.0 cm from soil line to top of foliage.
*Spread*.—Approximately 34.0 cm.
*Time and conditions to produce a rooted cutting*.—2 weeks.
*Life cycle*.—Annual.
*Flowering requirements*.—Blooms repeatedly from spring to fall.

Stems:
*General description*.—Round with lateral ridges.
*Stem color*.—Closest to RHS 144B (Yellow-Green).
*Anthocyanin color*.—Absent.
*Pubescence*.—Absent.
*Stem diameter*.—2.0 mm to 3.0 mm.
*Stem length*.—9.0 cm to 10.0 cm.
*Internode length*.—1.4 cm.
*Branching*.—Abundant.

Leaves:
*Arrangement*.—Alternate.
*Shape*.—Oblanceolate.
*Apex*.—Acute.
*Base*.—Rounded.
*Margin*.—Entire.
*Leaf attachment*.—Petiolate.
*Surface appearance* (*both surfaces*).—Dull, slightly waxy.
*Leaf length*.—3.2 cm.
*Leaf width*.—1.5 cm.
*Leaf thickness*.—Less than 1.0 mm.
*Surface texture* (*both surfaces*).—Dull, slightly waxy, soft.
*Leaf color*.—Upper surface: Closest to but darker than RHS 138A (Green). Lower surface: Closest to but darker than RHS 148C (Yellow-Green).
*Leaf surface pubescence*.—Absent.
*Venation*.—Only the mid vein is visible.
*Petiole*.—Absent.
*Fragrance*.—Absent.

Inflorescence:
*Inflorescence type*.—Solitary, sessile.
*Flowering habit*.—Determinate.
*Time to bloom from propagation*.—6 to 8 weeks.
*Lastingness of individual blooms on the plant*.—1 day.
*Flower diameter*.—3.6 cm.
*Flower depth*.—1.8 cm.
*Fragrance*.—Absent.

Flower bud:
*Surface appearance and texture*.—Shiny, pubescent.
*Shape*.—Lanceolate.
*Bud length*.—1.3 cm.
*Bud diameter*.—4.0 mm.
*Bud color*.—RHS 145A (Yellow-Green).

Corolla:
*Shape*.—Five distinct petals, free, petals are heart-shaped with a square base.
*Petal pubescence*.—Glabrous.
*Petal size*.—Length: 2.0 cm. Width: 1.4 cm.
*Petal apex*.—Retuse.
*Petal margin*.—Double lobed.
*Petal color* (*both surfaces*).—Closest to RHS 155C (White) but pure white.

Calyx:
*Arrangement*.—Composed of two sepals, free.
*Sepals*.—Shape: Elliptic. Apex: Cuspidate. Margin: Entire, slightly sinuate. Sepal length: 9.0 mm. Sepal diameter: 8.0 mm. Sepal color: Closest to RHS 144B (Yellow-Green) and translucent. Texture (both surfaces): Soft, dull and slightly sticky.

Reproductive organs: Androecium.
*Stamen number*.—Many.
*Stamen form*.—Free.
*Stamens color*.—Anther: RHS 17A (Yellow-Orange). Filament color: RHS 145D (Yellow-Green).
*Stamen length*.—5.0 mm.
*Pollen amount*.—Minimal.
*Pollen color*.—RHS 17A (Yellow-Orange).
*Fragrance*.—Absent.
*Placental arrangement*.—Central.
*Pistil number*.—1 (per inflorescence).
*Pistil length*.—1.1 cm.
*Stigma color*.—RHS 157D (Green-White).
*Stigma length*.—3.0 mm.
*Style length*.—8.0 mm.
*Style color*.—RHS 145D (Yellow-Green).
*Seed production*.—None observed.

Disease and insect resistance: None observed.

Environmental conditions, disease and insect resistance: None observed.

COMPARISON WITH PARENTAL LINES AND KNOWN VARIETY

'SAKPOR018' is a distinct variety of *Portulaca* owing to its white flower color and domed plant habit. 'SAKPOR018' is distinguished from its parents as shown below in Table 1.

TABLE 1

| Comparison with Parental Lines | | | |
|---|---|---|---|
| Characteristic | 'SAKPOR018' | Female parent: '7Bl-23A-V1' | Male parent: '7Bl-25A-V1' |
| Flower size | Medium | Smaller than 'SAKPOR018' | Medium |
| Plant growth habit | Domed | Domed | Upright |

'SAKPOR018' is most similar to the variety SUN DANCE 'White', also known as 'SAKPOR006' (U.S. Plant Pat. No. 24,526) however, there are differences in plant habit and petal color as described in the table below.

TABLE 2

| Comparison with Similar Variety | | |
|---|---|---|
| Characteristic | 'SAKPOR018' | 'SAKPOR006' |
| Plant growth habit | Domed, compact | Semi-mounding, upright and vigorous |
| Petal color | Both surfaces are closest to RHS 155C (White) but pure white | Upper surface: RHS N155A (White) with RHS 145D (Yellow-Green) at the base. Lower surface: RHS N155A (White) |

I claim:

1. A new and distinct variety of *portulaca* plant designated 'SAKPOR018' as illustrated and described herein.

* * * * *